United States Patent [19]
Krief

[11] 4,408,066
[45] Oct. 4, 1983

[54] METHYL CYCLOPROPANE-1,3-DICARBOXYLATE

[75] Inventor: Alain Krief, Wepion, Belgium

[73] Assignee: Roussel Uclaf, Paris, France

[21] Appl. No.: 308,026

[22] Filed: Oct. 2, 1981

[30] Foreign Application Priority Data

Oct. 10, 1980 [FR] France .................. 80 21690

[51] Int. Cl.³ .......................... C07C 69/757
[52] U.S. Cl. ................................. 560/124
[58] Field of Search ........................ 560/124

[56] References Cited

FOREIGN PATENT DOCUMENTS 53-84947  9/1978  Japan .................. 560/124

OTHER PUBLICATIONS

Devos, Tetrahedron Letters, 21 pp. 1847–1850 (1978).

Ueda, Agr. Biol. Chem., 34 pp. 1119–1125 (1970).
Crombie, J. Chem. Soc. (c), pp. 1076–1080 (1970).

*Primary Examiner*—Michael L. Shippen
*Attorney, Agent, or Firm*—Hammond & Littell, Weissenberger and Muserlian

[57] ABSTRACT

Novel methyl esters of cis or trans configuration in their optically active form of the formual

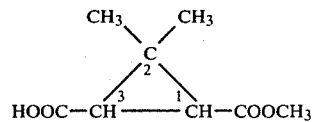

which are useful as intermediates for the preparation of pesticidal compounds and a process for their preparation and intermediates.

1 Claim, No Drawings

METHYL CYCLOPROPANE-1,3-DICARBOXYLATE

STATE OF THE ART

J.A.C.S., Vol. 76 (1954) p. 5257 describes the preparation of cis caronic acid by oxidation of a bicyclic diacetonic compound and gives physical constants for the corresponding methyl ester but the reference does not forsee the synthesis of the corresponding trans acid or its methyl ester. French Pat. No. 2,376,120 describes the preparation of alkyl esters of racemic 2,2-disubstituted-3-formyl-cyclopropane-1-carboxylic acids by reducing the acid function of a monoalkyl ester of the corresponding 2,2-disubstituted-cyclopropane-1,3-dicarboxylic acid followed by oxidation of the resulting alcohol group.

OBJECTS OF THE INVENTION

It is an object of the invention to provide the optically active isomers of the methyl esters of formula I.

It is another object of the invention to provide a novel process for the preparation of the optically active isomers of formula I and novel intermediates formed therein.

These and other objects and advantages of the invention will become obvious from the following detailed description.

THE INVENTION

The novel products of the invention are methyl esters of cis or trans configuration in their optically active form of the formula

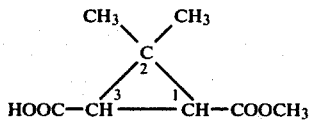

The preferred compounds of the invention are the monomethyl esters of (1R,3S) and (1S,3R)cis 2,2-dimethyl-cyclopropane-1,3-dicarboxylic acids and the monomethyl esters of (1R,3R) and (1S,3S)trans 2,2-dimethyl-cyclopropane-1,3-dicarboxylic acids.

The novel process of the invention for the preparation of the compounds of formula I comprises salifying the monomethyl ester of (1RS,3SR)cis 2,2-dimethyl-cyclopropane-1,3-dicarboxylic acid with d or l α-methyl-benzylamine, recovering the crystallized salt formed, dissolving the said salt in water, treating the solution with a mineral base and then with an acid to obtain either the monomethyl ester of (1R,3S)cis 2,2-dimethyl-cyclopropane-1,3-dicarboxylic acid or its (1S,3R)cis isomer depending on whether d or l α-methyl-benzylamine, respectively was used, if desired, reacting the latter with strong base to isomerize the monomethyl ester to the monomethyl ester of (1S,3S)trans 2,2-dimethyl-cyclopropane-1,3-dicarboxylic acid or (1R,3S)trans isomer, respectively.

In a preferred mode of the process of the invention, the salification with α-methyl-benzylamine is effected in acetone and the crystallization of the salt from acetone is effected in 2 steps. The mineral base is preferably an alkali metal carbonate or hydroxide such as potassium carbonate, sodium carbonate, dilute sodium hydroxide solution and dilute potassium hydroxide solution. The acid used is preferably a dilute inorganic acid such as dilute hydrochloric acid or dilute sulfuric acid. The strong base for the isomerization is preferably an alkali metal alcoholate such as sodium methylate, sodium ethylate or potassium tert.-butylate or an alkali metal hydride and is effected in an alcohol or ether.

The novel intermediate of the invention are the d and l α-methyl-benzylamine salts of the monomethyl esters of (1R,3S)cis and (1S,3R)cis 2,2-dimethyl-cyclopropane-1,3-dicarboxylic acids.

Until now, the resolution of esters of cis cyclopropane-1,3-dicarboxylic acids was not known and the interest in such a process resides in the fact that the resolution which is not possible in the case of the dicarboxylic acids becomes possible in the case of the monomethyl esters due to the existence of enantiomers caused by dissymetry of the molecule.

Moreover, the conversion of a derivative of a cis cyclopropane-dicarboxylic acid to the corresponding trans derivative has not been previously known and the process of the invention shows, in an unexpected manner, that it is possible to isomerize a compound of formula I with a (1R,3S) cis or (1S,3R)cis configuration into the analogous (1S,3S) trans or (1R,3R)trans isomer by treatment with a strong base without saponification of the ester group or a racemization.

The process of the invention is illustrated in the following reaction scheme:

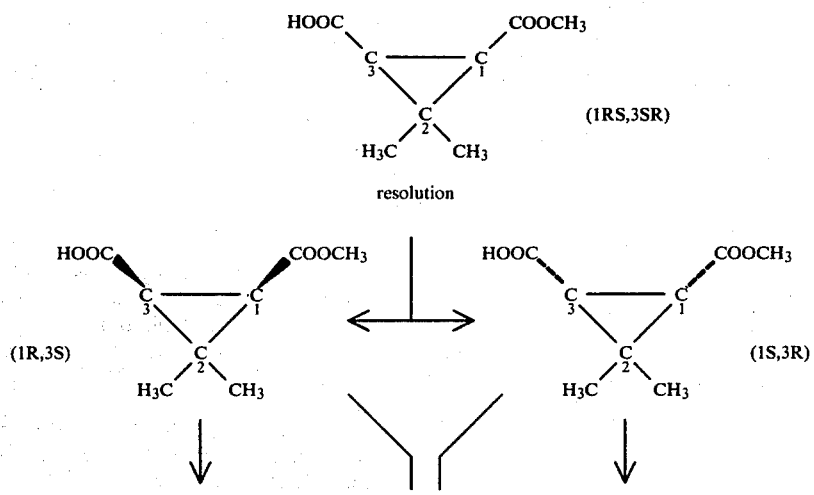

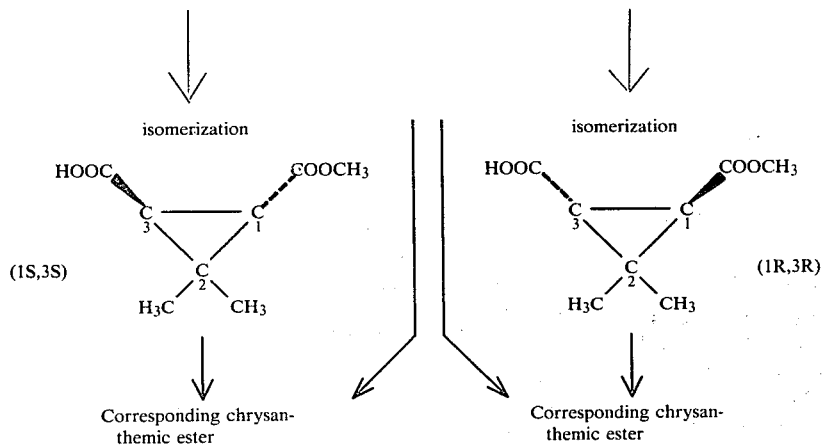

The compounds of formula I are useful intermediates and may be used in the synthesis of the corresponding chrysanthemic acid derivatives. It is possible to subject the compounds of formula I to a reduction of the acid function to the alcohol group, then oxidize the alcohol group to an aldehyde and subject the latter to the Wittig reaction with a triphenyl isopropyl phosphonium halide to obtain methyl chrysanthemate with the same configuration of the compound of formula I.

This series of reactions is illustrated in Example 5. French Pat. No. 2,376,120 illustrates a series of reactions of this type using racemic compounds.

It is well known that chrysanthemic acid esters are also useful as intermediates in the synthesis of other known esters possessing pesticidal activity such as insecticidal activity.

In the following examples there are described several preferred embodiments to illustrate the invention. However, it is to be understood that the invention is not intended to be limited to the specific embodiments.

EXAMPLE 1

Resolution of the mono methyl ester of (1RS, 3SR)cis 2,2-dimethyl-cyclopropane 1,3-dicarboxylic acid (a) Isolation of the mono ester of (1R,3S)cis acid.

3.7 g of d (+) α-methyl-benzylamine were added to a solution of 100 ml of acetone and 5.26 g of the monomethyl ester of (1RS,3SR)cis 2,2-dimethyl-cyclopropane-1,3-dicarboxylic acid and the mixture stood for 4 days at room temperature and was then filtered to remove crystals. The filtrate was evaporated to dryness and the residue was taken up in acetone. The solution was allowed to stand for 24 hours and was then filtered. The two groups of crystals were combined and the filtrate A was kept.

The crystals were dissolved in acetone and after initialization of crystallization, the mixture was allowed to stand for 3 days. The mixture was filtered and the crystals were dried to obtain 1.69 g of the benzylamine salt which was then dissolved in water. 1.03 g of potassium carbonate were added to the solution and the aqueous phase was washed with ether and was slightly acidified by addition of 10% hydrochloric acid solution. The mixture was extracted with ether and the ether phase was washed with water, then with aqueous sodium chloride solution, dried and evaporated to dryness to obtain 1 g of the monomethyl ester of (1R,3S)cis 2,2-dimethyl-cyclopropane-1,3-dicarboxylic acid with a melting point of 54° C. and a specific rotation of $[\alpha]_D^{25} = +30.92°$ (c=ethanol) which showed that the product consisted of 5.77% of the (1S,3R)cis isomer and 94.23% of the (1R,3S)cis isomer having the formula

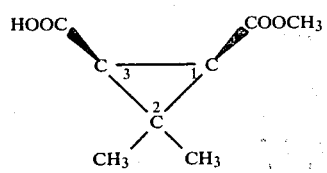

(b) Isolation of the mono ester of (1S,3R)cis acid

Filtrate A was evaporated to dryness and the crystalline material was treated as above to obtain a product consisting of 43% of the monomethyl ester of (1R,3S)cis 2,2-dimethyl-cyclopropane-1,3-dicarboxylic acid and 57% of the (1S,3R)cis isomer of the formula

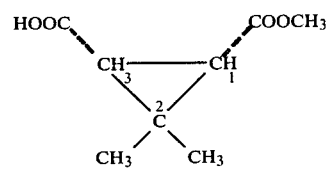

2.56 g of this mixture and 1.8 g of l (−) α-methyl-benzylamine were reacted as in Example 1 to obtain 0.813 g of the monomethyl ester of (1S,3R)cis 2,2-dimethyl-cyclopropane-1,3-dicarboxylic acid with a melting point of 53° C. and a specific rotation of $[\alpha]_D^{25} = -29.3°$ (c=ethanol) which was 92% of the (1S,3R)cis isomer and 8% of the (1R,3S)cis isomer.

NMR Spectrum (deuterochloroform): (1S,3R)cis isomer

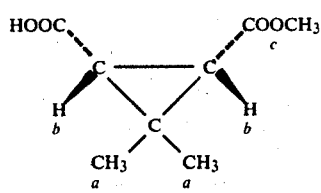

$\Delta H_a$=singulet at 1.28 ppm and at 1.40 ppm; $\Delta H_b$=singulet at 1.96 ppm; $\Delta H_c$=singulet at 3.70 ppm.

EXAMPLE 2

Isomerization of the mono methyl ester of (1S,3R)cis 2,2-dimethyl cyclopropane 1,3-dicarboxylic acid into corresponding ester of (1R,3R)trans acid A mixture of 0.516 g of the monomethyl ester of (1S,3R)cis 2,2-dimethyl-cyclopropane-1,3-dicarboxylic acid and 3 ml of a solution of 5 M sodium methylate in methanol was refluxed under an inert gas for 75 minutes and was then cooled to room temperature. 10% hydrochloric acid was added to the mixture to adjust the pH to 2 and the mixture was then extracted with ether. The organic phase was washed with water and then with aqueous saturated sodium chloride solution, dried and evaporated to dryness to obtain 0.36 g the monomethyl ester of (1R,3S)trans 2,2-dimethyl-cyclopropane-1,3-dicarboxylic acid with a specific rotation of $[\alpha]_D^{25} = -51.65°$ C. (c=ethanol). The isomerization was effected by the following reaction.

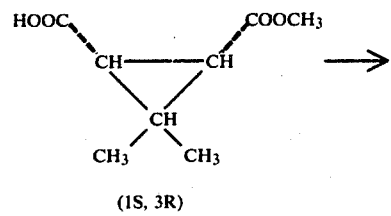

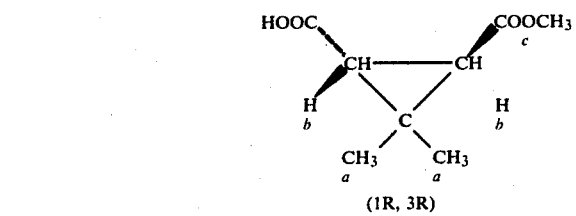

NMR Spectrum (deuterochloroform): $\Delta H_a$=singulet at 1.28 ppm and at 1.31 ppm; $\Delta H_b$=singulet at 2.23 ppm; $\Delta H_c$=singulet at 3.70 ppm.

EXAMPLE 3

Isomerization of the mono methyl ester of (1R,3S)cis 2,2-dimethyl cyclopropane 1,3-dicarboxylic acid into corresponding ester of (1S,3S)trans acid Using the procedure of Example 3, the monomethyl ester of (1R,3S)cis 2,2-dimethyl-cyclopropane-1,3-dicarboxylic acid was reacted to obtain the monomethyl ester of (1S,3S)trans 2,2-dimethyl-cyclopropane-1,3-dicarboxylic acid with a specific rotation of $[\alpha]_D^{25} = +51.66°$ (c=ethanol). The reaction proceded according to the reaction scheme

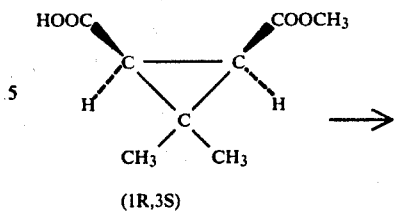

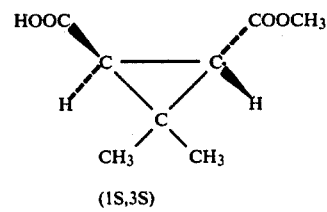

EXAMPLE 4

Methyl (1R,3S)cis chrysanthemate

STEP A: Methyl (1R,3S)cis 2,2-dimethyl-3-hydroxymethyl-cyclopropane-1-carboxylate 0.348 g of diborane in dimethyl sulfide (5.05×10$^{-3}$ moles) were added slowly under an inert atmosphere to a solution of 0.8 g of the monomethyl ester of (1R,3S)cis 2,2-dimethyl-cyclopropane-1,3-dicarboxylic acid in 20 ml of ether and the mixture was refluxed for one hour and then cooled to room temperature. 2 ml of methanol and then 10 ml of 10% hydrochloric acid were added to the mixture which was extracted with ether. The ether phase was washed with water, then aqueous saturated sodium chloride solution, dried and evaporated to dryness. The residue was chromatographed over silica gel and was eluted with ether to obtain 0.57 g of methyl (1R,3S)cis 2,2-dimethyl-3-hydroxymethyl-cyclopropane-1-carboxylate as the fraction with an Rf=0.7. The product had a specific rotation of $[\alpha]_D^{25} = -73.76°$ (c=ethanol).

IR Spectrum (ethanol): Absorption at 3050 to 3700 cm$^{-1}$ (OH)

NMR Spectrum (chloroform):

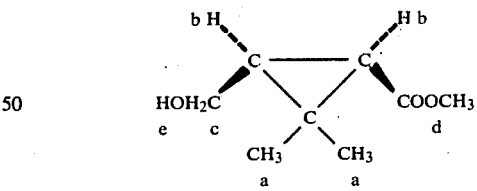

$\Delta H_a$=singulet at 1.16 ppm; $\Delta H_b$=multiplet of 1.24 to 1.56 ppm; $\Delta H_c$=massive at 3.20 ppm; $\Delta H_d$=singulet at 3.57 ppm; $\Delta H_e$=doublet center towards 3.78 ppm (J=7 Hz).

STEP B: Methyl (1R,3S)cis 2,2-dimethyl-3-formyl-cyclopropane-1-carboxylate

A solution of 0.54 g of the product of Step A in 7 ml of methylene chloride was added to a suspension of 1.105 g of a complex of chromic anhydride and pyridine hydrochloride (5.18×10$^{-3}$ mole) in 7 ml of methylene chloride and the mixture was stirred for 3 hours. 7 ml of ether were added to the mixture which was stirred for 2 hours and was filtered. The filter was washed several times with ether and the filtrate was evaporated to dryness. The residue was chromatographed over silica gel and was eluted with an 8-2 ether-pentane mixture to recover 0.48 g of methyl (1R,3S)cis 2,2-dimethyl-3-formyl-cyclopropane-1-carboxylate with an Rf=0.85 and a specific rotation of $[\alpha]_D^{25}= -82.15°$ (c=acetone)

IR Spectrum (Chloroform): Absorption at 1730 cm$^{-1}$ (ester carbonyl); at 1700 cm$^{-1}$ (aldehyde carbonyl).

NMR Spectrum (chloroform):

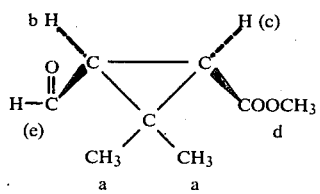

$\Delta H_a$=singulet at 1.24 ppm and 1.49 ppm; $\Delta H_b$=doublet center towards 1.7 ppm; $J_{b,c}$=8 Hz $J_{b,e}$=6 Hz; $\Delta H_c$=doublet center towards 2.01 ppm, J=8 Hz; $\Delta H_d$=singulet at 3.65 ppm; $\Delta H_e$=doublet center towards 9.58 ppm, J=6 Hz;

STEP C: Methyl (1R,3S)cis chrysanthemate 1.5 ml of a solution of 1.6 N butyllithium in hexane were added under an inert atmosphere to a suspension of 1.08 g of isopropyl triphenyl phosphonium iodide in 10 ml of tetrahydrofuran and the mixture was stirred for 10 minutes. Then, 0.34 g of the product of Step A were added to the mixture which was then stirred for 30 minutes and admixed with water. The mixture was extracted with ether and the organic phase was washed with water, then with aqueous saturated sodium chloride solution, dried and evaporated to dryness. The residue was chromatographed over silica gel and was eluted with a 1-9 ether-pentane mixture to obtain 0.19 g of methyl (1R,3S)cis chrysanthemate with an Rf=0.75 and a specific rotation of $[\alpha]_D^{25}= +57.840$ (c=acetone).

Various modifications of the products and process of the invention may be made without departing from the spirit or scope thereof and it is to be understood that the invention is intended to be limited only as defined in the appended claims.

What I claim is:

1. A compound selected from the group consisting of the salts of d and l α-methyl-benzylamine and the monomethyl esters of (1R,3S)cis and (1S,3R)cis 2,2-dimethyl-cyclopropane-1,3-dicarboxylic acid.

* * * * *

UNITED STATES PATENT AND TRADEMARK OFFICE
CERTIFICATE OF CORRECTION

PATENT NO. : 4,408,066

DATED : October 4, 1983

INVENTOR(S) : ALAIN KRIEF

It is certified that error appears in the above-identified patent and that said Letters Patent is hereby corrected as shown below:

Title page, line 2 of Abstract: "formual" should read

-- formula --.

Column 2, line 12: "(1R, 3S)" should read -- (1R, 3R) --.

Signed and Sealed this

Twenty-first Day of February 1984

[SEAL]

Attest:

GERALD J. MOSSINGHOFF

Attesting Officer     Commissioner of Patents and Trademarks